United States Patent [19]

Chang

[11] Patent Number: 6,007,206
[45] Date of Patent: Dec. 28, 1999

[54] COMB MIRROR FOR IMPROVING HEALTH OF A HUMAN BODY

[76] Inventor: Kwei-Tang Chang, No. 14, Lane 54, Luong Shuan St., Panchiao City, Taipei Hsien, Taiwan

[21] Appl. No.: 09/305,436

[22] Filed: May 6, 1999

[51] Int. Cl.⁶ .............................. G02B 5/08; G02B 7/182
[52] U.S. Cl. ......................... 359/850; 359/851; 359/855; 362/136
[58] Field of Search ................................... 359/850, 851, 359/854, 855, 856, 860, 589; 362/83.1, 136, 137, 139, 140

[56] References Cited

U.S. PATENT DOCUMENTS

| | | | |
|---|---|---|---|
| 4,242,587 | 12/1980 | Lescrenier | 250/491 |
| 4,918,579 | 4/1990 | Bennett | 362/32 |
| 4,925,285 | 5/1990 | Dowdell et el. | 359/855 |
| 5,625,501 | 4/1997 | Taggert | 359/855 |

*Primary Examiner*—Cassandra Spyrou
*Assistant Examiner*—Mohammad Y. Sikder
*Attorney, Agent, or Firm*—Rosenberg, Klein & Lee

[57] ABSTRACT

A comb mirror for improving health of a human body is disclosed. A plurality of far infrared ray lamps are installed in the inner space of the comb mirror body, By a first switch within the body, the first switch will control the on and off states of the far infrared ray lamps. A protecting web is installed in front of the inner space for isolating the far infrared ray lamps for providing the user to contact the far infrared rays lamps. Each of two sides of the body is installed with a respect mirror door which may rotate with the body. Each outer surface of the mirror door is installed with a plan mirror. The inner surface of the mirror seat is installed with concave mirror. By opening the mirror door, far infrared ray will be emitted. The concave mirror serves to focus the far infrared ray to the human body.

4 Claims, 4 Drawing Sheets

COMB MIRROR FOR IMPROVING HEALTH OF A HUMAN BODY

FIELD OF THE INVENTION

The present invention relates to a comb mirror for improving health of a human body, and especially to comb mirror suitable to be installed in a bathroom or other proper places, thereby, the comb mirror has the function of both beauty and health.

BACKGROUND OF THE INVENTION

In the prior art, a comb mirror in a bath room or bedroom is general a pure mirror with at most a cabinet on the rear side of the mirror for disposing some objects such as cosmetics, scraper, etc. No other functions are provided. However, health and beauty are more and more required for modern peoples. The conventional products about health and beauty can not meet the requirement of peoples. Some quick and well modern ways have been provided. Therefore, if the conventional comb mirror is improved to be combined with the functions of health and beauty, only other the functions of comb mirror are increased, but also no extra space is occupied.

SUMMARY OF THE INVENTION

Accordingly, the object of the present invention is to provide a comb mirror for improving health of a human body. The comb mirror body is installed with far infrared ray lamps. By a first switch to control the switching of the infrared ray lamps so as to emit far infrared ray which is beneficial to human body, a user may enjoy the advantages of the far infrared ray.

Another object of the present invention is to provide a comb mirror for improving health of a human body, wherein a concave mirror is installed in the comb mirror body for focusing the radiating far infrared ray and then reflecting the far infrared ray. Therefore, the user may be radiated by far infrared ray.

A further object of the present invention is to provide a comb mirror for improving health of a human body, wherein the comb mirror has illuminating lamps for illuminating.

A still object of the present invention is to provide a comb mirror for improving health of a human body with various sizes suitable to be installed in bathroom or bedroom, etc.

In order to achieve the aforementioned objects. The present invention provides a comb mirror for improving health of a human body. A plurality of far infrared ray lamps are installed in the inner space of the comb mirror body, By the first switch within the body, the first switch will control the on and off states of the far infrared ray lamps. A protecting web is installed in front of the inner space for isolating the far infrared ray lamps for providing the user not to contact the far infrared ray lamps. Each of two sides of the body is installed with a respect mirror door which may rotate with the body. Each outer surface of the mirror door is installed with a plan mirror. The inner surface of the mirror is installed with concave mirror. By opening the mirror door, far infrared ray will emit, the concave mirror serves to focus the far infrared ray to the human body.

The various objects and advantages of the present invention will be more readily understood from the following detailed description when read in conjunction with the appended drawing.

DETAILED DESCRIPTION OF THE PREFERRED EMBODIMENTS

Figure 1:
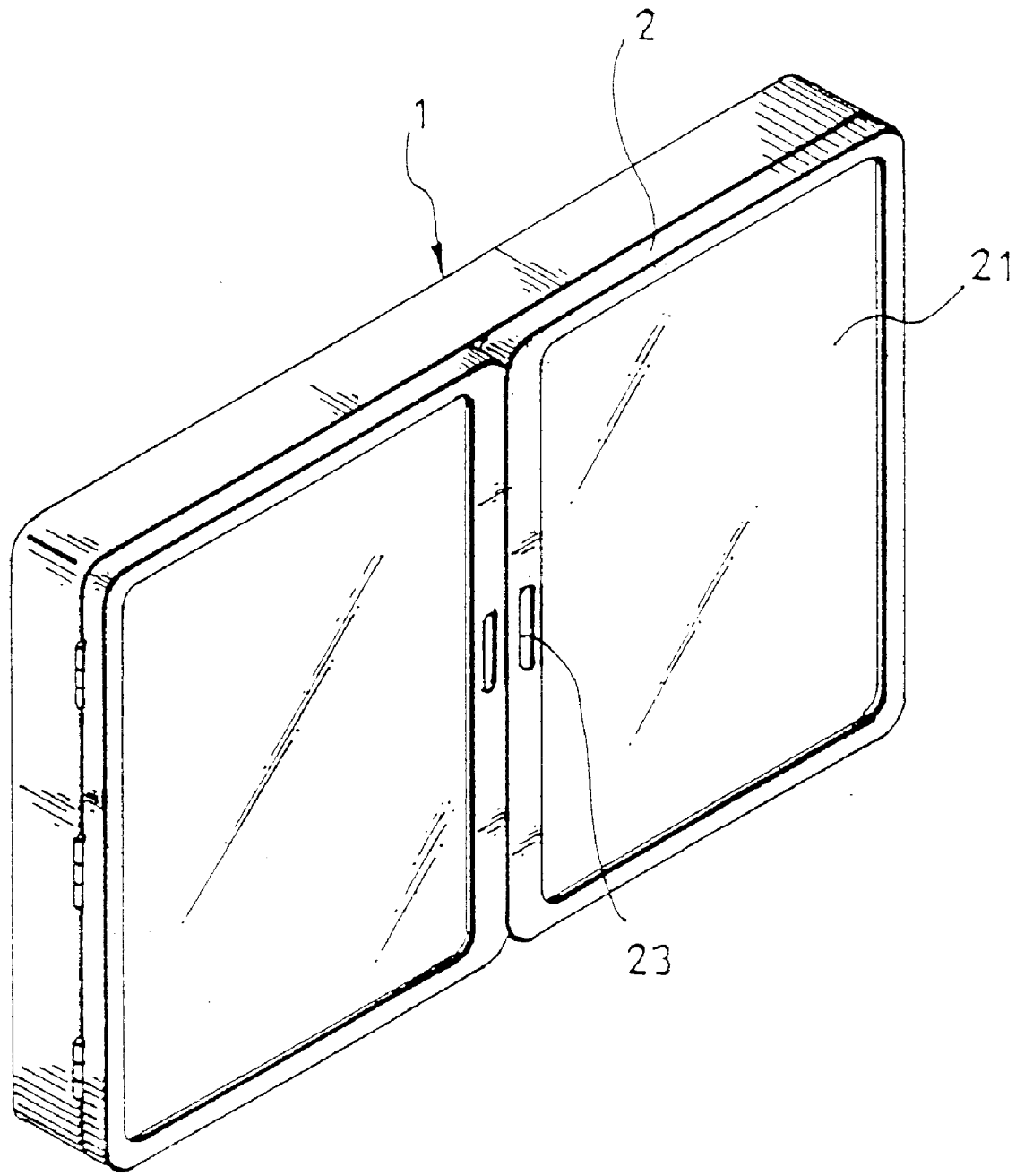
FIG. 1 shows a perspective view according to the present invention.
Figure 2:
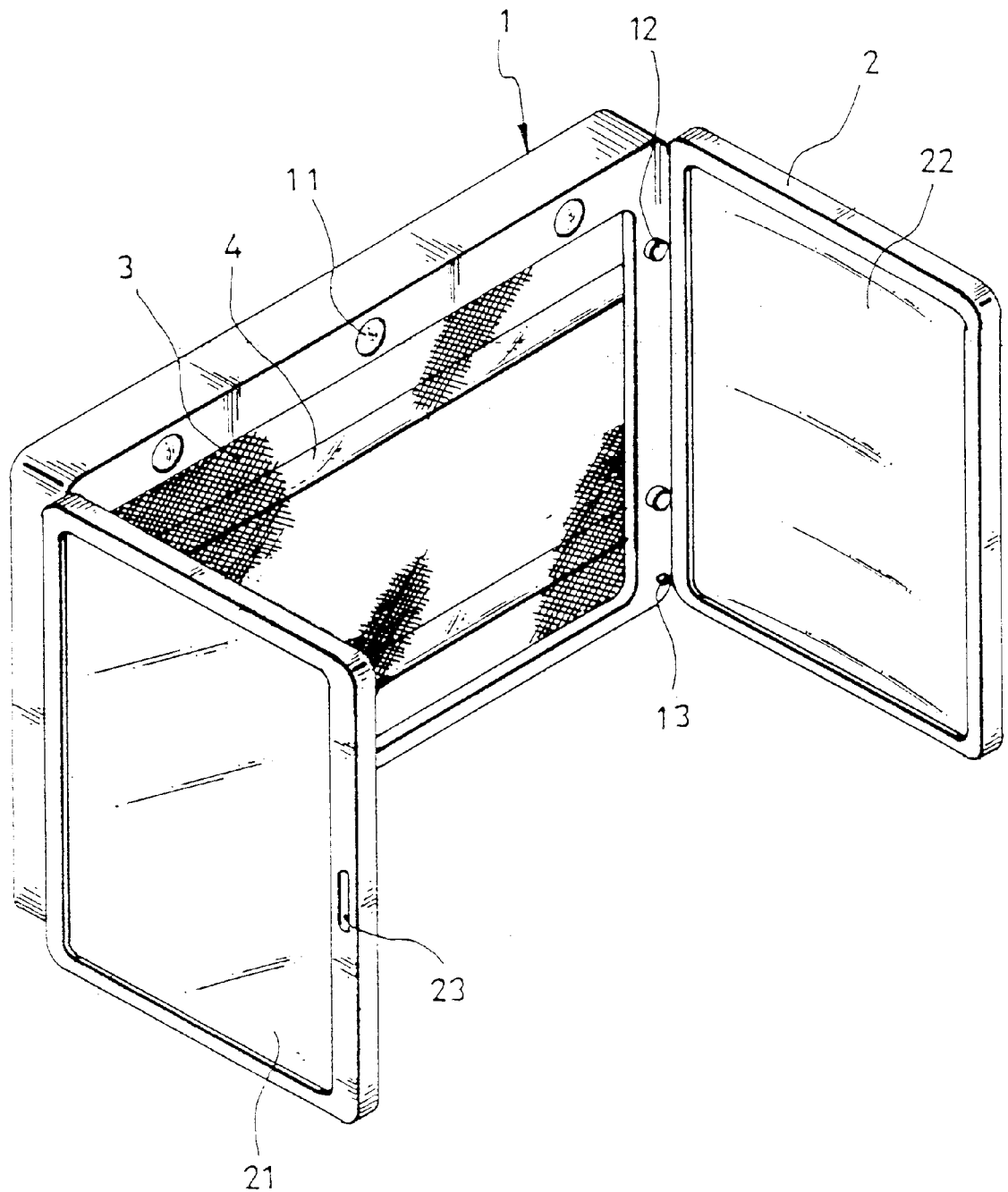
FIG. 2 is a perspective view showing the present invention, in which the mirror door is opened.
Figure 3:
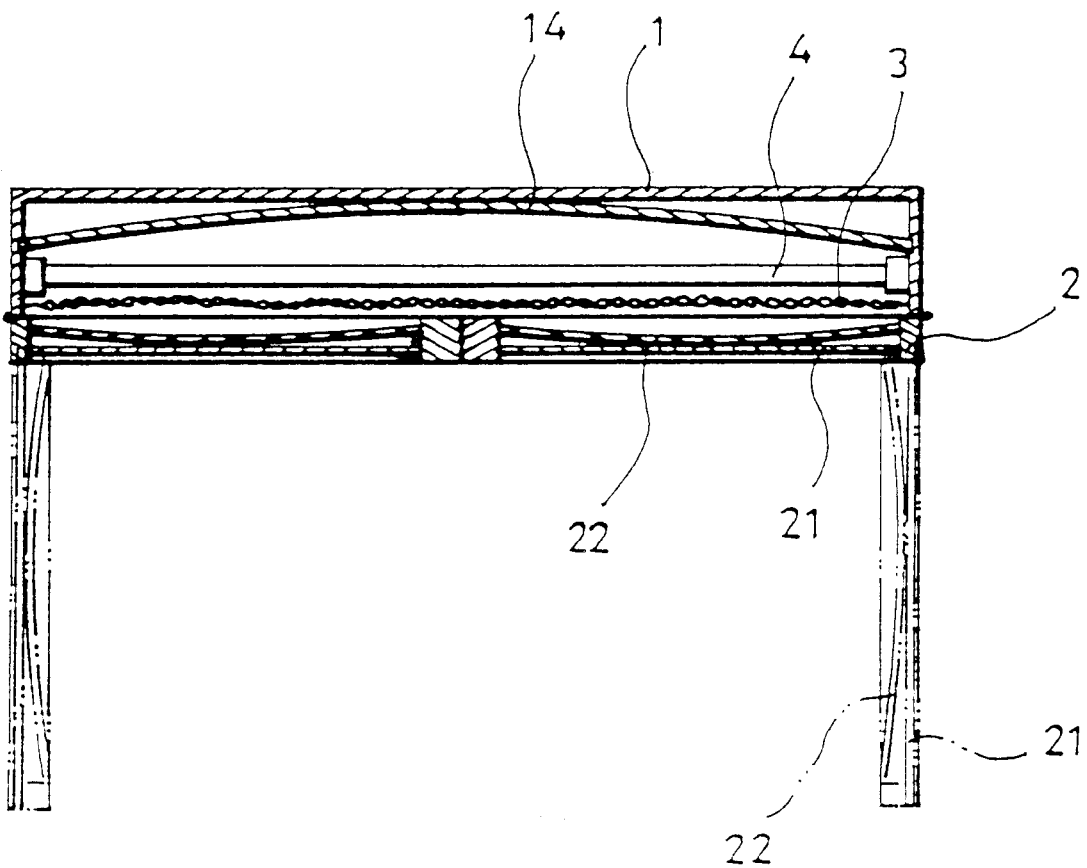
FIG. 3 is an upper perspective view showing the inner structure of the present invention.
Figure 4:
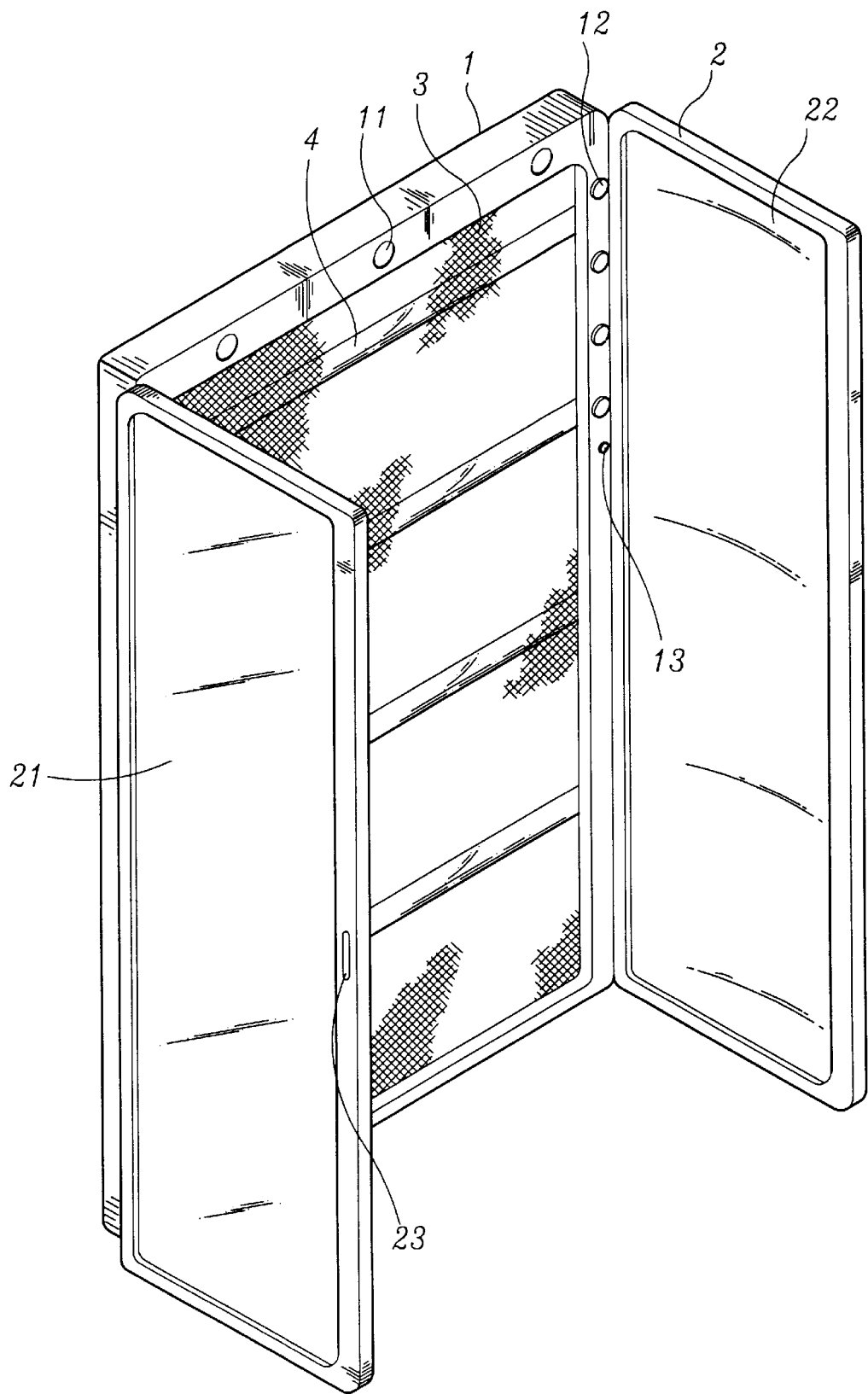
FIG. 4 shows embodiment of the present invention which contact with ground so that the user may view the whole body.

Referring now to FIGS. 1 and 3. the health comb mirror of the present invention is illustrated. The body 1 has an inner space. This inner space is sequentially installed with a reflector 14, a plurality of far infrared ray lamps 4, and a protecting web 3. Each of the two sides in front of the body 1 is pivotally installed with a respect mirror door 2 by hinges so that the two mirror doors may rotate with respect to the body 1 to open or close the inner space. A plan mirror 21 is installed on the outer surface of the mirror door 2 and a concave mirror 22 is installed on the inner surface of the mirror door 2. The outer surface of the mirror door 2 near the edge is installed with a concave handle 23. The plurality of far infrared ray lamp 4 are connected with respect first switches 12. The first switches 12 are arranged on the lateral side of the body 1. The first switch 12 serves to control the on and off states of the far infrared ray lamp 4. The protecting web 3 is employed to isolate the far infrared ray lamps 4 within the body 1 so to prevent the user to contact the lamp to be harmed by burning. In the present invention, a plurality of illuminating lamps 11 is disposed in front of the body 1, and the illuminating lamps 11 are connected to a press-able second switch 13 which is arranged in front of the body 1. When the aforementioned mirror door 2 is closed so that the mirror door 2 presses the second switch 13, the illuminating lamps 11 will be turned off. When the mirror door 2 is actuated so that the second switch 13 is not pressed, the illuminating lamps 11 will conduct and light for illumination. When the far infrared ray is not used. the two mirror doors 2 can be closed completely. The plan mirror 21 serves to reflect images. When the far infrared ray is serve to take care health, the mirror door 2 is opened and then to operate the second switch 12 so to actuate the far infrared ray lamp 4. Then, other than a part of the generated far infrared ray projects forwards, the remaining far infrared ray is focused by the concave mirror 22 so that the far infrared ray is enhanced to reflect to the body of the user, therefore, the object of health protection. Moreover, other than that shown in FIG. 1, the present invention may be designed as that shown in FIG. 4. which contact with ground. Thereby, the whole body of the user may be radiated by far infrared ray. Except that the size is larger than the prior art comb mirror, the other components are identical, thus, the detail thereof will not be described herein. Far infrared ray is a part of infrared ray and is electromagnetic wave, which is a kind of sun light and can not be seen by human visual ability. The far infrared ray is only the electromagnetic wave having the function of warming human cells. The qigong master may emit far infrared ray to human body for warming human cells. Thus, the user may feel comfort and the pulse and blood flowing are enhanced. Like a person strikes a bell, then the bell will vibrate due to oscillation. The far infrared ray is a periodic wave, which may act on the molecules of objects. A large number of organic materials oscillates within the frequency range of far infrared ray. Thus, these organic materials may oscillate with far infrared ray, and so dose the human body. In EM spectrum, the far infrared ray has a wavelength ranged from 3 to 1000 $\mu$, which is suitable to human body (6~14 μ). The far infrared ray is a safe EM wave and has a wavelength larger than that visual light. The far infrared ray may be transmitted to a desired object without air. Far infrared ray can impinge into the organization and warm the organization. By the periodic wave of the far infrared ray, the molecule will oscillate.

The far infrared ray has the following advantages for human health:

In the digest process of a human body, food is digested and then became the cells of the human body. In a series of digest process, the far infrared ray is a primary medium to actuate these reactions, i.e. the composition of cells, regeneration of cells, and activity of cells.

After cells are warmed by far infrared ray, the blood capillary will expand to enhance the circulation of blood and the regeneration of cells. The blood obstacles in body will be removed and thus the organ will regenerate. Thus, some diseases about heart are prevented in advance. The abilities of resisting spasm, suppressing the abnormality of consciousness nerves, etc. are enhanced.

The far infrared ray may adjust directly the self-control nerves, when hypophysis cerebri can not work well, the fatigue of nerves, low resistability, and diseases will occur. While these phenomenon can be resolved through being radiated by far infrared ray.

The far infrared ray has apparent effects to metabolism, such as power metabolism and material metabolism, the leaven growing, etc, Thus, the waste in body will be drained out with water from sweat glands and digest system. The oxidized reduction reaction is increased. Cancer cells is suppressed.

Far infrared ray ceramics have the effect of quick activating organic material with water (including biology, water, human body, wine, tea, . . . , etc). The higher the temperature, the quick the reaction. By sufficiently supplying with power, the conversion speed can be increased. Since the thermal energy between atoms is converted into light wave, this has no damage to ceramic object. While the radiated molecule does not been harmed by the far infrared ray. Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A comb mirror for improving health of a human body comprising:

a comb mirror body having an inner space, two respect sides of the inner space being installed with a mirror door, a pair of mirror doors being rotatable with respect to the comb mirror body so as to be opened or closed, each outer surface of said pair of mirror doors being installed with a plane mirror;

a plurality of far infrared ray lamps arranged above the comb mirror body, the lamps being connected to a first switch, the first switch being installed within the comb mirror body, wherein on and off states of the lamps being controlled by said first switch;

a protecting web arranged in front of the inner space of the comb mirror body for isolating the far infrared ray lamps and the comb mirror body so to prevent a user from contacting with the lamps.

2. The comb mirror for improving health of a human body as claimed in claim 1, wherein the mirror door has a concave mirror in the inner surface thereof.

3. The comb mirror for improving health of a human body as claimed in claim 1, wherein a reflector is installed in the inner space of the comb mirror body, which is located behind the far infrared ray lamps.

4. The comb mirror for improving health of a human body as claimed in claim 1, wherein a plurality of illuminating lamps are installed in front of the body, the illuminating lamps are installed with a second switch, the second switch is disposed in front of the comb mirror body, when the mirror door is closed so that the mirror door presses the second switch, the illuminating lamp will be turned off and then is distinguished, when the mirror door is closed so that the second switch is not contacted, then the illuminating lamp will conduct and illuminate.

* * * * *